US005762923A

United States Patent [19]

Gross et al.

[11] Patent Number: 5,762,923
[45] Date of Patent: Jun. 9, 1998

[54] STABILIZED INTERFERON ALPHA SOLUTIONS

[75] Inventors: Günter Gross, Weil am Rhein, Germany; Sabino Del Terzo, Allendale; Saran Kandakuri Kumar, Edison, both of N.J.

[73] Assignee: Hoffmann-La Roche Inc., Nutley, N.J.

[21] Appl. No.: 627,563

[22] Filed: Apr. 4, 1996

[30] Foreign Application Priority Data

Apr. 6, 1995 [EP] European Pat. Off. ............ 95105166

[51] Int. Cl.$^6$ .................. A61K 37/66; A61K 38/21; A61K 38/19; C07K 14/52
[52] U.S. Cl. .................. 424/85.7; 424/85.1; 530/388.23
[58] Field of Search .................. 424/85.7, 85.1

[56] References Cited

U.S. PATENT DOCUMENTS 5,503,827  4/1996  Woog et al. .................. 424/85.1

FOREIGN PATENT DOCUMENTS

| 0284249 | 9/1988 | European Pat. Off. |
| 0 396 777 | 11/1990 | European Pat. Off. |
| 0 440 100 | 8/1991 | European Pat. Off. |
| 0593868 | 4/1994 | European Pat. Off. |
| 61/277633 | 12/1986 | Japan |
| WO 89/04177 | 5/1989 | WIPO |
| WO 94/26302 | 11/1994 | WIPO |
| WO94/26302 | 11/1994 | WIPO |

OTHER PUBLICATIONS

Patent Abstracts of Japan, vol. 11, No. 139, JP61277633, Toray Ind. Inc. (Dec. 8, 1986).
English Abstract for Document B1 (61/277633).
Abstract corresponding to EP 0 440 100.

*Primary Examiner*—Cecilia J. Tsang
*Assistant Examiner*—Michael Borin
*Attorney, Agent, or Firm*—George W. Johnston; William H. Epstein; John P. Parise

[57] ABSTRACT

An aqueous interferon composition which comprises an amount of interferon-alpha dissolved in water with a non-ionic detergent and benzyl alcohol in amounts sufficient to stabilize the amount of interferon-alpha, which composition contains an amount of acidic buffer which provides a pH of 4.5 to 6.0, and may also contain an isotonizing agent.

9 Claims, No Drawings

STABILIZED INTERFERON ALPHA SOLUTIONS

BACKGROUND OF THE INVENTION

The present invention relates to an aqueous solution of interferon alpha which is suitable for parenteral administration. The manufacture of interferon solutions involves a number of problems which are caused by the sensitivity of the active ingredient against physical and chemical influences and which hitherto could not be solved satisfactorily. Like other proteins interferon in aqueous solutions is subject to chemical degradation mechanisms such as proteolysis, oxidation, disulfide exchange, oligomerization, deamidation and beta-elimination, and physical mechanisms such as aggregation, precipitation and adsorption. Interferon solutions therefore contain additives which are to counteract these effects. For instance, human serum albumin (HSA) is used in commercial preparations as a stabilizer which, however, is problematic in view of the danger of viral contamination and formation of aggregates which in turn may cause antibody formation. Therefore, interferon solutions have already been proposed which avoid the use of HSA and which contain other auxiliary agents, inter alia, non-ionic detergents (cf the International Patent Application WO 89/04177 and Japanese Patent Publication 61-277633). International Patent Application WO 94/26302 discloses stabilized liquid pharmaceutical compositions comprising gamma interferon. It is further known that the maintenance of particular pH values is important for the stability of interferon solutions. For instance, a pH range of 4.0–6.0 is mentioned in patent application WO 30 89/04177. Finally, as in other injection solutions further excipients can be required, e.g., agents for adjusting an isotonic solution, and preserving agents.

Since interferon is highly active and is present in minimal concentration in pharmaceutical preparations, the stability of interferon preparations and guaranteeing a constant concentration of the active ingredient is of particular importance. It has been found that in order to guarantee optimal utilization properties the excipients of an interferon solution must be selected carefully from a multitude of potentially suitable agents and be harmonized with each other. For example, the adsorption of interferon-alpha 2a on glass surfaces has a maximum at pH 5–6 so that this pH would in principle seem unfavorable. On the other hand, covalent degradation reactions proceed through a minimum at this pH. Commercial HSA-stabilized solutions have pH 7. The utilization properties of interferon solutions are influenced by a number of non-correlating factors in an unpredictable manner.

SUMMARY OF THE INVENTION

It has now been found that aqueous HSA-free interferon-alpha solutions containing (a) an interferon-alpha;

(b) a non-ionic detergent;

(c) a buffer for adjusting pH 4.5–6.0;

(d) benzyl alcohol; and, optionally, (e) an isotonizing agent;

exhibit optimal utilization properties, i.e. storage stability and bioavailability of the declared amount of active ingredient. Thus, the present invention is an aqueous interferon composition which comprises an amount of interferon-alpha dissolved in water with a non-ionic detergent and benzyl alcohol in amounts sufficient to stabilize the amount of interferon-alpha, which composition contains an amount of buffer which provides a pH of 4.5 to 6.0. This aqueous composition may also include an isotonizing agent in an amount sufficient to render the composition isotonic.

DETAILED DESCRIPTION OF THE INVENTION

Any known interferon-alpha can be used to make an aqueous stabilized composition of the present invention, for example, interferon-alpha as disclosed in European Patent No. 43980 (referred to therein as mature human leukocyte interferon-A, see also J. Pharm. Biomed. Analysis Vol. 7, No. 2, 233–238 (1989)).

Interferon alpha as defined in this invention includes interferon alpha conjugated to a polymer such as a polyalkylene glycol (substituted or unsubstituted), for example polyethylene glycol, to form PEG-interferon alpha. Conjugation may be accomplished by means of various linkers known in the art, in particular by linkers such as those disclosed in European patent publication EP-A-0510356, A-15 0593868, Monfardini et al., Bioconjugate Chemistry, 6:62–69 (1995); and available from Shearwater Polymers, Inc. (Huntsville Ala.) as described in their catalogue. The molecular weight of the polymer, which is preferably polyethylene glycol, may range from 300 to 50,000 daltons, preferably 10,000 to 50,000 daltons, and one or more, preferably one to three, polymers may be conjugated to the interferon alpha. A preferred interferon-alpha conjugate is formed using interferon alpha 2a.

A preferred interferon-alpha for use in any of the aqueous compositions of the present invention is interferon-alpha 2a and PEGylated (PEG) interferon-alpha 2a. Interferon alpha 2a is a well known protein which may be obtained by conventional methods such as protein synthesis or recombinant technology. Interferon alpha 2a is disclosed for example in EP 43980; Maeda et al. PNAS 77:7010 (1980); Levy et al. PNAS 77:5102 (1980); Levy et al. PNAS 78:6186 (1981).

Preferably, the aqueous compositions in accordance with the present invention contain about $10^6$–$10^8$ International Units (IU) interferon-alpha per ml, 1 to $36\times10^6$ IU/ml is usual. A preferred solution contains about 18 to about $36\times10^6$ IU of interferon alpha per ml. pH may be about 4.0 to 6.0. Preferred solutions have a pH of about 4.9 to 5.1. Pegylated interferon alpha compositions may in particular have a pH of 6.0. The amount of buffer is about 10–15 mmolar of any conventional buffer which will provide the desired pH, which pH may be determined by conventional methods. A preferred amount of non-ionic detergent in the aqueous compositions is about 0.01 to about 0.5 mg/ml. "About" is used in the sense that a skilled person would consider sufficient to provide the aqueous compositions of this invention.

The aqueous compositions of this invention contain an amount of a non-ionic detergent and benzyl alcohol sufficient to stabilize the amount of interferon alpha in the composition. Amounts sufficient to stabilize may be determined by conventional methods for determining stability, such as activity after storage, or concentration after storage. For example, compositions may be stored for three months at 25 or 35 degrees C. and the amount of interferon alpha present may then be determined by conventional methods such as HPLC. The higher the percentage of intact interferon in the solution after storage the better is the stabilizing effect.

Examples of non-ionic detergents for use in the preparations in accordance with the invention are Polysorbates, such as e.g. Polysorbate 20 or Polysorbate 80

(polyoxyethylene(20)sorbitan monooleate). The amount of detergent in the solutions in accordance with the invention is preferably about 0.01–0.5 mg/ml, preferably 0.05–0.2 mg/ml. Preferred buffer substances are sodium or ammonium acetate, and sodium lactate. Acetic acid and/or sodium hydroxide may be included. The concentration of these buffer substances is preferably about 10–15 mmolar. Preferably, the interferon solutions in accordance with this invention are adjusted to pH 5.0 + or −0.1, or pH 6.0 + or −0.1. Benzyl alcohol is contained in the solutions in accordance with this invention in an amount of about 8–20 mg/ml, particularly 10 mg/ml. As isotonizing agents there come into consideration in particular sodium chloride, mannitol, glycerol and amino acids, particularly arginine, lysine, histidine and methionine, as well as ethanolamine. Sodium chloride or mannitol are preferred. The amount of these auxiliary agents which is required for achieving isotonicity depends on the composition of the solution and can be determined with ordinary skill. For example, that a solution is isotonic may be determined by measuring, the freezing point depression of the solution (Remington's Pharmaceutical Sciences, A. R. Gennaro, ed., Mack Publishing Company, Easton, Penn. 18042, 17th edition (1985) p. 221–229 and p. 1455–1472).

Thus, an aqueous composition of this invention may comprise interferon-alpha 2a (in unmodified or PEGylated form), polyoxy-ethylene(20)sorbitan monooleate, benzyl alcohol, ammonium acetate or sodium lactate; and, in an amount sufficient to provide an isotonic solution, sodium chloride, mannitol, glycerol, arginine, lysine, histidine, methionine, or ethanolamine.

In a preferred aqueous composition of this invention, the amount of interferon alpha 2a is about $1–36\times10^6$ IU/ml, the amount of polyoxyethylene (20) sorbitan monooleate is 0.2 mg/ml, the amount of ammonium acetate or sodium lactate is 10 mM, the amount of benzyl alcohol is 10 mg/ml, and the isotonizing agent is sodium chloride in an amount sufficient to render the composition isotonic. In another preferred composition, the amount of PEG interferon alpha 2a is about $1–36\times10^6$ IU/ml or $1–18\times10^6$ IU/ml, the amount of polyoxyethylene (20) sorbitan monooleate is 0.05 mg/ml, the buffer is 13 mM ammonium acetate, the amount of benzyl alcohol is 10 mg/ml, and the isotonizing agent is mannitol or sodium chloride in an amount sufficient to render the composition isotonic. In another preferred aqueous composition, the amount of PEG-interferon alpha 2a is $1–36\times10^6$ or $1–18\times10^6$ IU/ml, the amount of benzyl alcohol is 10 mg/ml, the buffer is 2.617 mg/ml sodium acetate and 0.462 mg/ml glacial acetic acid, the amount of polyoxyethylene (20) sorbitan monooleate is 0.05 mg/ml, and the isotonizing agent is sodium chloride.

The invention is further illustrated but not limited by the Examples which follow.

EXAMPLE 1
Preparation of PEG-IFN alpha 2a

PEGylation: IFN-alpha 2a was dialyzed twice against 10 liters of a buffer consisting of 5 mM sodium acetate pH 5.0 containing 120 mM NaCl. One gram of material (7.26 mg/ml) was PEGylated using a 3:1 molar ratio of solid PEG reagent alpha-methyl-omega-[2-[[(3-methyl-2-pyridinyloxy)carbonyl]amino]ethoxy]poly(oxy-1,2-ethanediyl) SRU 110. The pH of the solution was adjusted by adding one-tenth volume of 100 mM sodium borate pH 10.7. Following a one hour incubation at room temperature, the reaction was quenched by addition of 1 M glycine to a final concentration of 20 mM glycine. One twentieth volume of 1 M sodium acetate, pH 4.0 was added to achieve a final pH of 5.0–6.0. The protein solution was diluted fourfold with buffer consisting of 40 mM ammonium acetate pH 4.5.

Purification: The diluted PEGylation mixture was loaded onto a 333 ml CM-cellulose column equilibrated with 40 mM ammonium acetate pH 4.5 at a flowrate of 19 ml/min. PEGylated interferon was eluted with a 0–250 mM NaCl gradient over 8 column volumes. Fractions containing PEG-IFN were pooled according to the results of SDS-PAGE. The final pool contained 291 mg at 0.831 mg/ml. Pooled material was concentrated to 3.96 mg/ml via an Amicon stirred cell ultrafiltration unit using a YM10 (MW cutoff 10000) membrane.

Concentrated material (238 mg) was loaded onto a 6.3 L S-200 gel filtration column equilibrated with 40 mM ammonium acetate and 125 mM NaCl. The flowrate was 20 ml/min. Fractions were collected and analyzed via SDS-PAGE. The S-200 column pool contained 480 ml at 0.48 mg/ml. An aliquot of the S-200 column pool was concentrated to 8.7 mg/ml using an Amicon stirred cell. This material was used to prepare the formulations of Examples 4 and 5.

Pegylation Bulk interferon alpha 2a (interferon) is diafiltered at 4° C. to remove ammonium ions and to increase the pH to 9.0. The interferon is first concentrated to 8 mg/mL and is subsequently diafiltered with 25 volumes of 50 mM borate, pH 9.0. The final concentration of IFN is 8 mg/mL. PEG2-NHS 40kDa pegylation reagent (Monfardini, supra) from Shearwater Polymers, Inc. (Huntsville, Ala.) is dissolved in 4° C. 1 mM HCl and immediately added to the diafiltered interferon. The ratio of reagent to protein is 3:1. The ratio of hydrochloric acid to diafiltered interferon is 1:2 such that the final reaction mixture concentration of interferon is 5 mg/mL. The reaction proceeds for 2hr at 4° C. The mixture is stirred. The reaction is stopped by adding glacial acetic acid to lower the reaction pH to 4.5. The reaction mixture is then diluted 10-fold with water. The water is at room temperature.

Separation A column packed with EMD Fractogel COO is used for separation of PEGylated interferon (PEG-IFN) from oligo-PEG-IFN and unmodified interferon. The loading capacity of this resin is 3 mg/mL. The linear velocity of the separation is 1.3 cm/min. The column is run at room temperature. The column is equilibrated in 20 mM sodium acetate, pH 4.5. After sample loading, the column is washed with 20 mM sodium acetate, pH 4.5, 10 mM NaCl, pH 4.5. This step removes the pegylation reagent and byproducts and some of the oligo-PEG-IFN species. After this step is complete, the column is then washed with 20 mM sodium acetate, pH 4.5, 200 mM NaCl, pH 4.5. This is the product elution step. Finally, the unmodified interferon is removed by 20 mM sodium acetate, 750 mM NaCl, pH 4.5. The column is subsequently sanitized with 0.5 M NaOH, followed by a water rinse and a 200 mM sodium acetate, pH 4.5 wash.

Final Diafiltration PEG-IFN is eluted in the 200 mM NaCl step from the CM column. The PEGylated interferon (PEG-IFN) is diafiltered against 5 volumes of 20 mM sodium acetate, pH 6.0, containing 50 mM NaCl. This material was used to prepare the formulation of Example 6.

EXAMPLE 2

Interferon Solution

| Ingredient | amount per ml |
| --- | --- |
| Interferon-alpha 2a | $1-36 \times 10^6$ IU |
| Ammonium acetate | 0.77 mg |
| Sodium chloride | 7.21 mg |
| Benzyl alcohol | 10.0 mg |
| Polysorbate 80 | 0.2 mg |
| Acetic acid ad pH 5.0 ± 0.1 | q.s. |
| NaOH 0.1 N ad pH 5.0 ± 0.1 | q.s. |
| Water for injection | ad 1.0 ml |

Manufacturing procedure:

The formulations were prepared under aseptic conditions in a laminar flow bench in 50 ml sterile polypropylene tubes with srew cap. The excipients were dissolved in water for injection, the pH was adjusted and the solutions were gassed with nitrogen. Then, Interferon bulk solution was added under gentle stirring, followed by an adjustment of the pH, if necessary, and the adjustment to the final volume by addition of water for injection. The solutions were sterile filtered into a fresh polypropylene tube using a low protein binding 0.2 μm filter and filled into 2 ml vials of glass type I. The vials were flushed with nitrogen and closed with a butyl rubber stopper, which was laminated with an inert film of fluoropolyethylene.

EXAMPLE 3

Interferon Solution

| Ingredient | amount per ml |
| --- | --- |
| Interferon-alpha 2a | $1-36 \times 10^6$ IU |
| Ammonium acetate | 0.77 mg |
| Glycerol | 20.0 mg |
| Benzyl alcohol | 10.0 mg |
| Polysorbate 80 | 0.2 mg |
| Acetic acid ad pH 5.0 ± 0.1 | q.s. |
| NaOH 0.1 N ad pH 5.0 ± 0.1 | q.s. |
| Water for injection | ad 1.0 ml |

Manufacturing procedure: as in Example 2.

EXAMPLE 4

Interferon Solution

| Ingredient | Amount per ml |
| --- | --- |
| PEG-Interferon-alpha 2a | $1-18 \times 10^6$ IU |
| Ammonium acetate | 1.0 mg |
| Sodium chloride | 5.0 mg |
| Benzyl alcohol | 10.0 mg |
| Polysorbate 80 | 0.05 mg |
| Acetic acid ad pH 5.0 ± 0.1 | q.s. |
| NaOH 0.1 N ad pH 5.0 ± 0.1 | q.s. |
| Water for injection | ad 1.0 ml |

Manufacturing procedure: as in Example 2.

EXAMPLE 5

Interferon Solution

| Ingredient | Amount per ml |
| --- | --- |
| PEG-Interferon-alpha 2a | $1-18 \times 10^6$ IU |
| Ammonium acetate | 1.0 mg |
| Sodium chloride | 3.0 mg |
| Mannitol | 30.0 mg |
| Benzyl alcohol | 10.0 mg |
| Polysorbate 80 | 0.05 mg |
| Acetic acid ad pH 5.0 ± 0.1 | q.s. |
| NaOH 0.1 N ad pH 5.0 ± 0.1 | q.s. |
| Water for injection | ad 1.0 ml |

Manufacturing procedure: as in Example 2.

EXAMPLE 6

Interferon Solution

| Ingredient | Amount per ml |
| --- | --- |
| PEG-Interferon-alpha 2a | $1-18 \times 10^6$ IU |
| Benzyl alcohol | 10 mg |
| Sodium chloride | 8.0 mg |
| Sodium acetate trihydrate* | 2.617 mg |
| Acetic acid (glacial)* | 0.0462 mg |
| Polysorbate 80** | 0.05 mg |
| Water for injection | q.s. 1.0 ml |

*the above ratio of these ingredients will provide a final pH of 6.0 ± 0.1.
**added as 2% w/w solution.

Manufacturing procedure: as in Example 2

For comparison purposes, the interferon-alpha 2a solutions of Example 2 with $3\times10^6$ IU IFN-alpha-2a (A/3), $6\times10^6$ IU IFN-alpha-2a (A/6), $9\times10^6$ IU IFN-alpha-2a (A/9), $18\times10^6$ IU IFN-alpha-2a (A/18) and $36\times10^6$ IU IFN-alpha-2a (A/36) and corresponding solutions without benzyl alcohol (B/3-36) were prepared according to the manufacturing procedure given in Example 2 and stored in the dark at 5°, 25° and 35° C. The contents of interferon-alpha-2a in the vials was determined after 3 months of storage. Samples were filtered through a 0.45 μm filter and analyzed by reverse phase HPLC for the remaining pure interferon-alpha-2a. The HPLC method has a standard deviation of about 5%. In this trial, IFN-alpha-2a of a purity of about 96% was used. The results of the storage trial is set out in Table 1. The percentage figures refer to the amount of pure IFN-alpha-2a in the stored solutions compared to the total amount of protein present at the beginning of the experiment.

TABLE 1

| Solution/ $\times 10^6$ IU IFN alpha 2a per ml | Contents of IFN alpha 2a in % after 3 months storage at | | |
| --- | --- | --- | --- |
| | 5° C. | 25° C. | 35° C. |
| A/3 | 93.8 | 60.7 | 43.5 |
| A/6 | 91.2 | 73.9 | 54.6 |
| A/9 | 94.1 | 80.3 | 61.6 |
| A/18 | 94.1 | 84.5 | 69.0 |
| A/36 | 91.9 | 88.5 | 71.1 |
| B/3 | 81.0 | 41.0 | 8.2 |
| B/6 | 88.9 | 55.1 | 8.5 |

TABLE 1-continued

| Solution/ × 10⁶ IU IFN alpha 2a per ml | Contents of IFN alpha 2a in % after 3 months storage at | | |
|---|---|---|---|
| | 5° C. | 25° C. | 35° C. |
| B/9 | 89.1 | 63.3 | 25.8 |
| B/18 | 92.2 | 62.8 | 26.8 |
| B/36 | 95.2 | 72.8 | 41.2 |

The better storage stability of the solution A is particularly evident at increased storage temperature.

In analogy, a solution of pegylated IFN of Example 4 with 3×10⁶ IU pegylated interferon-alpha-2a (C/3) and a corresponding solution without benzyl alcohol (D/3) were prepared and stored for 24 months at 5° and 25° C. The results of the storage trial are shown in Table 2.

TABLE 2

| Solution/ × 10⁶ PEG IU IFN alpha 2a per ml | Contents of PEG IFN alpha 2a in % after 24 months storage at | |
|---|---|---|
| | 5° C. | 25° C. |
| C/3 | 79.6 | 55.8 |
| D/3 | 60.1 | 5.8 |

The better storage stability of solutions which were prepared with the addition of benzyl alcohol is evident from these trials also.

EXAMPLE 7

As mentioned above, HSA-free solutions of interferons are known from the International Patent Application WO 89-04177 and the Japanese patent publication 61-277633. The stability of the solutions according to the invention was compared with the stability of interferon-alpha-2a solutions which were prepared in analogy to these known solutions. Solutions of the following composition were prepared:

| Solution X | |
|---|---|
| Interferon-alpha 2a | 3–36 × 10⁶ IU |
| Ammonium acetate | 0.77 mg |
| Sodium chloride | 8.77 mg |
| Polysorbate 80 | 0.3 mg |
| Acetic acid ad pH 5.0 ± 0.1 | q.s. |
| NaOH 0.1 N ad pH 5.0 ± 0.1 | q.s. |
| Water for injection | ad 1.0 ml |
| Solution Y | |
| Interferon-alpha 2a | 3–36 × 10⁶ IU |
| Succinic acid | 0.27 mg |
| Di-Sodium succinate | 0.73 mg |
| D-Mannitol | 40.0 mg |
| Polysorbate 80 | 0.1 mg |
| HCl 0.1 N ad pH 5.0 ± 0.1 | q.s. |
| NaOH 0.1 N ad pH 5.0 ± 0.1 | q.s. |
| Water for injection | ad 1.0 ml |

The solutions X and Y correspond to solutions described in the above documents, with 3,6,9,18 and 36×10⁶ IU interferon-alpha-2a being used instead of interferon-beta or interferon-gamma. The results obtained after 3 months at various storage temperatures are set out in Table 3 hereinafter

TABLE 3

| Solution/ × 10⁶ IU IFN alpha 2a | Contents of IFN alpha 2a in % after 3 months storage at | | |
|---|---|---|---|
| | 5° C. | 25° C. | 35° C. |
| X/3 | 72.5 | 13.7 | 0.0 |
| X/6 | 72.8 | 3.1 | 0.0 |
| X/9 | 83.7 | 42.6 | 1.7 |
| X/18 | 86.5 | 50.5 | 2.6 |
| X/36 | 88.0 | 54.1 | 4.5 |
| Y/3 | 67.1 | 32.7 | 0.0 |
| Y/6 | 80.0 | 53.5 | 0.0 |
| Y/9 | 84.9 | 63.4 | 4.3 |
| Y/18 | 89.0 | 59.5 | 13.7 |
| Y/36 | 90.7 | 60.0 | 18.9 |

From these data it is evident that when applying the technology described in the above-mentioned documents of the state of the art to interferon-alpha-2a no acceptable storage stability can be achieved.

We claim:

1. A human serum albumin-free aqueous interferon composition which comprises about $10^6$–$10^8$ IU/ml of interferon-alpha dissolved in water with a non-ionic detergent and 8 to about 20 mg/ml of benzyl alcohol which composition contains an amount of buffer which provides a pH of 4.5 to 6.0 and is characterized by absence of human serum albumin.

2. An aqueous interferon composition of claim 1 which contains an isotonizing agent in an amount sufficient to provide an isotonic solution.

3. An aqueous interferon composition of claim 1 wherein the pH is from pH 4.9–pH 5.1.

4. An aqueous interferon composition of claim 1 wherein the amount of interferon-alpha is about $10^6$–$10^8$ IU/ml; the amount of non-ionic detergent is about 0.01–0.5 mg/ml; and the amount of buffer is about 10–15 mmolar.

5. An aqueous interferon composition of claim 2 wherein the interferon-alpha is interferon-alpha 2a or PEG-interferon alpha 2a; the non-ionic detergent is polyoxyethylene(20) sorbitan monooleate; the buffer is selected from ammonium acetate and sodium lactate; and the isotonizing agent is selected from sodium chloride, mannitol, glycerol, arginine, lysine, histidine, methionine, and ethanolamine in an amount sufficient to provide an isotonic solution.

6. An aqueous interferon composition of claim 5 wherein the amount of interferon-alpha 2a is 1–36×10⁶ IU/ml; the amount of polyoxyethylene(20)sorbitan monooleate is 0.2 mg/ml; the amount of ammonium acetate or sodium lactate is 10 mM, the amount of benzyl alcohol is 10 mg/ml; and the isotonizing agent is sodium chloride.

7. An aqueous interferon composition of claim 5 wherein the interferon-alpha is PEG-interferon alpha 2a in the amount of 1–36×10⁶ IU/ml; the amount of polyoxyethylene (20)sorbitan monooleate is 0.05 mg/ml; the buffer is 13 mM ammonium acetate; the amount of benzyl alcohol is 10 mg/ml; and the isotonizing agent is sodium chloride or mannitol.

8. An aqueous interferon composition of claim 7 wherein the PEG-interferon alpha 2a is in the amount of 1–18×10⁶ IU/ml.

9. An aqueous interferon composition of claim 2 wherein the interferon-alpha is PEG-interferon alpha 2a in the amount of 1–18×10⁶ IU/ml; the amount of benzyl alcohol is 10 mg/ml; the buffer is 0.462 mg/ml glacial acetic acid and 2.617 mg/ml sodium acetate; the amount of polyoxyethylene (20) sorbitan monooleate is 0.05 mg/ml; and the isotonizing agent is sodium chloride.

* * * * *